United States Patent [19]

Benes

[11] 4,113,850
[45] Sep. 12, 1978

[54] COMPOSITION FOR THE DIAGNOSTIC VISUALIZATION OF NEOPLASTIC TISSUES

[75] Inventor: Ivan Benes, Greifensee, Switzerland

[73] Assignee: Solco Basel AG, Basel, Switzerland

[21] Appl. No.: 572,701

[22] Filed: Apr. 29, 1975

[30] Foreign Application Priority Data

Apr. 30, 1974 [CH] Switzerland ............... 5885/74

[51] Int. Cl.$^2$ ............... A61K 29/00; A61K 43/00
[52] U.S. Cl. ............... 424/1; 424/1.5; 424/9
[58] Field of Search ............... 424/1, 9, 1.5; 260/429 R

[56] References Cited

U.S. PATENT DOCUMENTS

| 3,466,361 | 9/1969 | Richards et al. ............... 424/1 |
| 3,749,556 | 7/1973 | Barak et al. ............... 424/1 X |

OTHER PUBLICATIONS

Sarin et al, Journal of Inorganic and Nuclear Chemistry, vol. 34, No. 1, Jan., 1972, pp. 581-590.
Ando et al, Nuclear Science Abstracts, vol. 29, No. 10, May 31, 1974, p. 2366, abstract No. 24540.
Markovits et al, Inorganic Chemistry, vol. 11, No. 10, Oct. 1972, pp. 2405-2408.
Zeidler et al, Nuclear Science Abstracts, vol. 29, No. 8, Apr. 30, 1974, p. 1812, abstract No. 18716.
Schneider, Journal of Nuclear Medicine, vol. 14, No. 11, Nov. 1973, pp. 843-845.

*Primary Examiner*—Benjamin R. Padgett
*Assistant Examiner*—Christine M. Nucker
*Attorney, Agent, or Firm*—Wenderoth, Lind & Ponack

[57] ABSTRACT

The present invention relates to an injectable complex used for the diagnostic visualization of neoplastic tissues i.e., tumors and metastases, by means of tissue scintigraphy, said injectable complex consisting essentially of $^{99m}$Technetium with a dicarboxylic or tricarboxylic acid of the general formula:

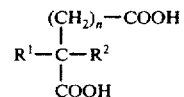

in which $n$ is 1 or 2, $R^1$ and $R^2$ taken together are an oxo group or a $>$CH—COOH group or $R^1$ is hydrogen or hydroxyl or an amino group and $R^2$ is hydrogen or one of the following groups:

—CH$_2$—COOH; —CHOH—COOH; —CO—COOH, and a water-soluble salt of the same, in a sterile aqueous solution having a physiologically harmless pH value.

8 Claims, No Drawings

COMPOSITION FOR THE DIAGNOSTIC VISUALIZATION OF NEOPLASTIC TISSUES

Various chemical compounds of short-lived radionuclides such as $^{99m}$Technetium and recently also $^{111}$Indium are used among others in nuclear medicine in diagnosing various illnesses, morphological-pathological changes in tissues and anomalies in the blood circulation.

Because of their short life (the physical half-life of $^{99m}$Technetium is 6 hours and that of $^{111}$Indium is 2.81 days) these isotopes and their compounds must be produced near their place of use.

$^{99m}$Technetium is produced by the radioactive decay of its mother isotope $^{99m}$Molybedenum; $^{111}$In is made from cadmium in a cyclotron. In practice the daughter isotope $^{99m}$Tc is made and isolated with the aid of so-called radionuclide generators, directly at the place where the material is to be labelled and used. In the generation of $^{99m}$Tc, the daughter isotope is eluted as the pertechnetate ($TcO_4^-$) with physiological salt solution (0.9%). In the pertechnetate $^{99m}$Tc is 7-valent.

To prepare the $^{99m}$Tc derivatives, $^{99m}$Tc-pertechnetate is reduced from the 7-valent level to a lower valency level, usually to 4-valent $^{99m}$Tc. The literature lists ascorbic acid, iron(II) ions, tin(II) chloride, sodium borohydride, electrolytic reduction and other reducing agents.

$^{111}$In among others is also used in various forms in nuclear medical diagnosis, e.g. as $^{111}$In(III) chloride.

Early and clearly positive evidence of malignant tumors or metastases would certainly be one of the most important objects of nuclear medical diagnosis; the depicting or visualization of neoplastic tissues by the administration of a radioactive material would be the simplest and for the person under investigation also the most considerate method of making a diagnosis.

The radiopharmaceuticals used for these diagnoses up to now, such as $^{75}$Se-sodium selenite, $^{67}$Gallium citrate or $^{203}$Hg-chlormerodrin or $^{197}$Hg-chlormerodrin, show a low and uncertain tumor affinity together with a high ray dose for the person examined. In addition, none of the preparations labelled with $^{99m}$Tc or $^{113m}$In which have been tried up to now show a clear and convincing specific affinity for neoplastic tissues, i.e. tumor and metastase tissues. If the prior art is viewed in its entirety it can be seen that a pronounced affinity for tumors has not been achieved up to now. Another source confirms that an absolutly tumor-specific radiopharmaceutical is still unknown [Dtsch. med. Wschr. 97, 1258 (1972)].

It was thus all the more surprising to find that an injectable complex of $^{99m}$Tc or $^{111}$In demonstrated a very high specific affinity for tumor and metastase tissues which had not even been approached previously, and thus represents in sterile aqueous solution of pH value of between 3.6 and 8.6 a preferable means for the visualization of neoplastic tissues by tissue scintigraphy.

The means of the invention consists essentially of an injectable complex of $^{99m}$Technetium or $^{111}$Indium with a dicarboxylic or tricarboxylic acid of the general formula:

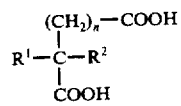

in which $n$ is 1 or 2, $R^1$ and $R^2$ together are an oxygen atom or the >CH—COOH group or $R^1$ is a hydrogen atom or a hydroxyl or amino group and $R^2$ is a hydrogen atom or one of the following groups:

—$CH_2$—COOH; —CHOH—COOH; —CO—COOH, or with a water soluble salt of the same, the binding in the complex being such that at least one valency of the technetium or indium ion is satisfied by a carboxyl group, in sterile aqueous solution of physiologically harmless pH value.

A dicarboxylate or tricarboxylate from the group isocitrate, cis-aconitate, alpha-ketoglutarate, oxalosuccinate, citrate, aspartate, oxaloacetate, malate and glutamate is preferred as the ligand of the central metal ion ($^{99m}Tc^{4+}$ or $^{111}In^{3+}$). Nevertheless other dicarboxylates and tricarboxylates encompassed by the general formula given above are also suitable as ligands.

The complex can also contain the complexly bound tin(II), tin(IV, iron(II) or iron(III) ion. Furthermore, it can also contain the sodium, potassium and/or calcium ion as salts of the non-complexed carboxyl groups.

The $^{99m}$Tc and $^{111}$In complexes with the ligands defined above surprisingly show a very high specific affinity for neoplastic tissues (tumors and metastases) as they concentrate in these tissues significantly more than in healthy tissue in the same organs or parts of the body. This therefore makes a clear and precise scintigraphic diagnosis of primary tumors and metastases possible for the first time.

The specific affinity of this radioactive complex may also be characterised in more detail by the following observations:

1. The highest concentration of activity can be seen particularly in the tumors and metastases in brain and bone tissue.
2. The concentration of activity in the tumors and metastases, particularly in brain and bone tissue, takes place only a few minutes after administration;
3. The concentration of activity in the tumors and metastases remains constant for some hours after administration, after which the activity decreases with a long effective half-life;
4. Complex which is not concentrated in the neoplastic tissues is, owing to its short biological half-life, relatively rapidly excreted from healthy tissue and the blood system through the kidneys.

The extraordinary specificity of the concentration of activity in tumor and metastases tissue is most simply shown by determining the so-called tumor brain quotient. With humans there are two different tumor brain quotients, an internal and an external quotient. The second is measured with the living patient (i.e. in vivo) by comparing the count rates over diseased and normal brain areas (regions of interest). The internal tumor brain quotient on the other hand is measured either after the death and autopsy of the patient who has been treated with the radiopharmaceutical shortly beforehand, or on an operation preparation after operative removal of a brain tumor.

This specificity is impressively demonstrated by the comparison with the radioactive compounds used up to now shown in tables 1 and 2.

Table 1

| Radionuclide or compound | Human external tumor brain quotient (in vivo) | Literature source |
|---|---|---|
| $^{99m}TcO_4$ | 1.7 : 1 | 1 |
| $^{99m}TcO_4$ | 1.3 : 1 | 2 |
| $^{99m}TcO_4$ | 1.2 – 2.5 : 1 | 3 |
| $^{197}Hg$-Chlormerodrin | 1.2 – 8.7 : 1 | 4 |
| $^{197}Hg$-Chlormerodrin | 1.2 – 3.1 : 1 | 5 |
| $^{113m}In$-DTPA | 2.2 : 1 | 1 |
| $^{75}Se$ | 2.0 – 5.0 : 1 | 6 |
| $^{99m}Tc$-Sn-citrate | 8 – 12 : 1 | according to the invention |

1) J. nucl. Med. 10, 18 (1969)
2) J. nucl. Med. 10, 34 (1969)
3) Arch. Psychiat. Nervenkr. 213, 200 (1970)
4) J. nucl. Med. 9, 16 (1968)
5) J. nucl. Med. 7, 32 (1966)
6) J. nucl. Med. 7, 197 (1966)

Table 2

| Radionuclide or compound | Human internal tumor brain quotient (after autopsy or on an operation preparation) | Literature source |
|---|---|---|
| $^{169}Yb$ | 1.8 – 5.0 : 1 | 1 |
| $^{99m}TcO_4$ | 1.8 – 5.3 : 1 | 1 |
| $^{99m}TcO_0 - 4.3 : 1$ | | 2 |
| $^{99m}Tc$-Sn-citrate | 112 : 1 | according to the invention |

1) J. nucl. Med. 10, 553 (1969)
2) Arch. Psychiat. Nervenkr. 213, 200 (1970)

As a result of its high specific affinity and rapid excretion from healthy tissue and the blood system the complex subjects the whole body and individual organs to a significantly lower dose of radioactive rays than the radiopharmaceuticals hitherto used. Now a selective concentration leads to the organs concerned receiving a higher ray dose. The acceptable ray dose to such organs is a limiting factor in the size of the radioactivity dose administered, and these organs are therefore termed "critical organs". These relationships can be concretely illustrated using the best investigated example, $^{99m}Tc$-pertechnetate. Pertechnetate behaves in a similar way to iodine or iodides in the body, so that particularly high concentrations occur in the thyroid but also in the plexus chorioideus (brain), in the salivary glands and in the gastric mucosa. It is these organs therefore which dictate the upper limit of the permissible radioactivity dose for the person to be investigated.

The following table gives the size of ray dose (in mrad/mCurie) of the more important organs for the hitherto most used radioactive substances and for the diagnostic means of the invention.

Table 3

| Radionuclide or compound | Ray dose of the critical organs in mrad/mCurie | | | | | |
|---|---|---|---|---|---|---|
| | Blood | Colon | Bladder | Thyroid | Kidney | Stomach |
| $^{99m}TcO_4$ | 17 – 47 | 150 – 290 | — | 100 – 270 | — | 40 – 320 |
| $^{197}Hg$-Chlormerodrin | — | — | — | — | 4370 – 19400 | — |
| $^{113m}In$-DTPA | 34 – 69 | — | 510 – 550 | — | 60 | — |
| $^{99m}Tc$-EDTA | — | — | 550 | — | 42 | — |
| $^{169}Yb$-DTPA | — | — | 390 | — | — | — |
| $^{99m}Tc$-Sn-citrate according to the invention | — | 126 | 342 | 0.19 | 38.4 | 0.25 |

The comparison shows an appreciably lower ray dose from the injectable complex of the invention; in the case of the thyroid and the gastric mucosa the dose is even approx. 100 times lower for the person investigated.

The lower ray dose, which is impressively lower for the critical organs listed above, represents a significant technical advance in the use of the injectable complex of the invention.

Compared with $^{99m}Tc$-pertechnetate, the complex possesses the further distinctive advantage that it can be administered direct, without preliminary treatment of the person to be investigated. It has already been mentioned that pertechnetate concentrates above all in the thyroid. If organs other than the thyroid are to be checked for possible tumors or metastases, as will usually be the case, the concentration of the pertechnetate in the thyroid must first be prevented. This is done by blocking the thyroid by the administration of potassium perchlorate or Lugol's solution (iodine solution); this also blocks the function of the thyroid for some time however. With the complex of the invention, not only is the necessity for preliminary treatment eliminated, but also the disadvantage that the breakdown in the functioning of the thyroid lasts for some time after the investigation.

In the diagnostic means of the invention the radioactive central metal ion is bound in a complex, i.e. masked, and thus outwardly chemically unreactive. As a result no exchange occurs in this case with the system or particular organs — in contrast to radioactive iodine in the thyroid. Because of its chemical inactivity the complex does not become tightly bound to the plasma proteins, this explaining the rapid distribution within the body and the relatively rapid excretion through the kidneys. As with the other means hitherto used or tried in radiodiagnosis, the concentration effect underlies non-specific mechanisms which are obviously of the same sort.

According to the invention there is now a reliable method for the diagnostic visualization of neoplastic tissues using tissue scintigraphy. In this method the complex described above is administered in sterile aqueous solution of physiologically harmless pH value to the person to be investigated, preferably intravenously, and the local amount of radioactivity determined with a scintillation counter or a gamma-ray camera.

A simple process has also been found by which the immediate preparation of the injectable radioactive complex can be carried out in one operation. This process is a further object of the invention.

The process of the invention consists essentially of introducing an aqueous solution of a dicarboxylic acid or tricarboxylic acid of the above formula or a salt of the same (a) as such or (b) with addition of a tin(II) salt or as a corresponding tin(II) complex into ampoules, rubber-capped serum vials, carpoules or disposable syringes, removing the solvent subsequently from the solution, reacting the intermediate product obtained which is in solid, stable form immediately before its use for diagnostic purposes with an aqueous solution containing the desired radioactivity dose of a $^{99m}$Technetium or $^{111}$Indium salt in the case of the intermediate product resulting from (a), or with an aqueous solution containing the desired radioactivity dose of a $^{99m}$Tc-pertechnetate or $^{111}$Indium salt in the case of an intermediate product resulting from (b), and if necessary adjusting the pH before or after the reaction to a physiologically harmless value, a co-complex with the tin ion being obtained in case (b), oxygen being excluded when working with a $^{99m}$Technetium salt or a $^{99m}$Tc-pertechnetate, and the sterility of the complex being ensured by starting with sterile solutions and working under sterile conditions, or by sterile filtering directly into sterile ampoules, rubber-capped serum vials, carpoules or disposable syringes, or by sterilising only after the introduction into the said vessels.

When carrying out the process in practice the dicarboxylic or tricarboxylic acid can be added as such and if necessary the pH adjusted — before or after the reaction with the radioactive salt solution — to the desired value by adding a base (sodium hydroxide solution) for example. The starting materials can however also be a water-soluble, non-toxic salt of the dicarboxylic or tricarboxylic acid, e.g. the sodium, potassium or calcium salt, and the pH can be corrected if necessary — before or after the reaction with the radioactive salt solution — by adding hydrochloric acid for example. With both these processes the complex is obtained as a complex salt of the corresponding cation; the sodium, potassium or calcium ion, whether added as a base to adjust the pH or as a salt of the dicarboxylic or tricarboxylic acid, is bound to the non-complexed carboxyl groups.

Various embodiments of the process will now be described.

According to a first embodiment, the starting material is a radioactive technetium salt or indium salt. Now technetium is usually available as a chemically stable 7-valent compount, the pertechnetate — normally sodium pertechnetate. It must therefore first be reduced to $^{99m}$Tc$^{4+}$, suitable methods for which have already been mentioned in the introduction. Owing to the sensitivity to oxydation of the technetium pas d'espace (IV) ion, the process should be carried out under conditions which exclude a possible oxydation back to the 7-valent state. A first possibility for doing this is to purge the solutions with an inert gas such as nitrogen, argon, carbon dioxide, nitrous oxide, or mixtures of the same. When an alkali metal salt or a calcium salt of the dicarboxylic or tricarboxylic acid is used as starting material, purging would naturally not be carried out with carbon dioxide. In general one works under an atmosphere of nitrogen. A second possibility for avoiding the oxidation of the technetium(IV) ion is offered by chemical antioxidants such as ascorbic acid, or dehydroascorbic acid and their water-soluble salts or 1-phenyl-3-pyrazolidone which are added to the solution.

The usual form of an indium salt is indium(III) chloride. This compound is only stable in relatively strongly acid solution, otherwise indium hydroxide precipitates out. This fact makes correction of the pH in every case essential so that the indium complex formed in acid solution can be injected without hazard. Sodium hydroxide solution for instance is used for adjusting the pH. The pH correction can be made both before or after formation of the complex. If it is made before formation of the complex, precipitation of indium hydroxide soon begins and the reaction mixture must be warmed for a time after the addition of the dicarboxylic or tricarboxylic acid chosen as ligand, and the reaction allowed to run for correspondingly longer. Because it represents the simpler and quicker procedure the pH is preferably not adjusted to the desired value until after the formation of the complex.

If an alkali metal salt, e.g. the sodium salt, of the dicarboxylic or tricarboxylic acid is the starting material rather than the free acid, then the solution is already alkaline, or even strongly alkaline if the previous reduction of the pertechnetate has been carried out with sodium borohydride. When an alkali metal salt is used a pH correction is not always necessary in the case of the technetium(IV) ion, but after a sodium borohydride reduction the too strongly alkaline pH must be adjusted to a physiologically harmless value by the addition of acid, e.g. hydrochloric acid. In the case of the indium ion or indium chloride the use of an alkali metal salt of the dicarboxylic or tricarboxylic acid is sometimes sufficient to neutralize the originally relatively strongly acidic solution.

According to a second embodiment of the process a pertechnetate or radioactive indium salt is reacted with the dicarboxylic or tricarboxylic acid or an alkali metal salt of the same in the presence of a water-soluble tin(II) salt, e.g. $SnCl_2$, or with a tin(II) complex of the said acids.

Particularly suitable tin(II) complexes are among others tri-tin-di-isocitrate, tri-tin-di-cis-aconitate, tin alpha-ketoglutarate, tri-tin-di-oxalosuccinate, tri-tin-di-citrate, tri-iron-tri-tin-tetra-citrate, tin asparate, tin oxaloacetate, tin malate and tin glutamate. In every case a co-complex with the tin ion is formed.

As a result of the very high sensitivity of the tin(II) ion to oxygen or oxydation, it is essential when using a pertechnetate to purge the solutions with an inert gas or treat them with an antioxidant. Suitable inert gases and antioxidants have already been mentioned.

In this embodiment the pertechnetate is reduced in one operation to $^{99m}$Tc$^{4+}$ which is converted directly thereafter to the desired complex. Owing to the particular simplicity of the procedure, this embodiment is preferred especially for the preparation of the technetium complexes. Even in this embodiment the possibly necessary correction of the pH value can be made before or after the formation of the technetium complex; it is advantageous to adjust the pH after forming the tin(II) complex, i.e. before reacting the tin(II) complex with the pertechnetate.

Then the water or solvent is removed from the solution of the compound which is to be reacted with the pertechnetate, technetium salt or indium salt. This is preferably done by freeze-drying (lyophilization). The above-mentioned solution includes in particular the tin(II) complex solution already prepared, that of the alkali metal salts or other salts of the dicarboxylic or tricarboxylic acid, and quite generally the solution of the compound intended as ligand and ready for use in the subsequent reaction, i.e. in particular after adjustment of the pH.

The intermediate products obtained as solids in this way are naturally far less sensitive than their solutions to chemical influences and particularly to oxydation, this above all being of considerable importance with tin(II) complexes. When the necessary precautions are carried out correctly (inert gas atmosphere and complete removal of water) a tin(II) complex lyophilized in this way can be kept for at least 6 months without change, or stored or transported. The stability of the intermediate product achieved in this way enables the radioactive complex to be prepared on the spot and directly before administration to the person under investigation, but at the same time also ensures a practically quantitative reaction with the pertechnetate or indium salt.

This also leads to the further advantage that a smaller liquid volume, measured exactly according to wish, can be administered. The final volume of the injectable complex solution is substantially that of the pertechnetate or indium salt solution used in the reaction. Now the administration of a diagnostic substance in relatively small volumes is quite desirable. In addition the reaction producing the radioactive complex proceeds more rapidly and more completely if it takes place in relatively concentrated solution.

The following directions for preparation, kept in general terms, illustrate the above remarks by means of a practical example.

Starting for example from isocitric acid or from one of its water-soluble, non-toxic salts, this is dissolved in water and the resulting solution purged with nitrogen. Tin(II) chloride or another tin(II) salt is added portionwise to this solution with stirring and further purging. The resulting solution can also be stabilised against autooxidation by adding a stabilizer e.g. ascorbic acid. After dissolution, the pH of the solution is adjusted to a physiologically harmless value and the solution immediately lyophilized or dried in some other way. Directly thereafter, or at a later time, possibly after transport or storage, the lyophilized tin(II) complex is mixed directly with the pertechnetate or radioactive indium solution, thus rapidly forming an intravenously administrable radioactive complex in aqueous solution.

The process of the invention can be particularly simply, rapidly and elegantly carried out with a sterile rubber-capped serum vial, which simultaneously serves as the reaction vessel and contains the freeze-dried stabilized specific tin(II) complex under an inert gas atmosphere.

EXAMPLE 1

50 g solid tin(II) chloride is added portionwise to 2.0 g isocitric acid in 20 ml water in a reaction vessel while stirring and passing nitrogen through the solution. When the tin(II) chloride has dissolved the solution is diluted to about 80 ml with water saturated with nitrogen and the pH adjusted to 6 ± 0.5 with 2N sodium hydroxide solution. The volume of the solution is then made up to 100 ml with water for injection which has been purged with nitrogen, and 1.0 ml portions of the resulting solution introduced into rubber-capped serum vials under an atmosphere of nitrogen. To prepare the $^{99m}$Tc-isocitrate complex, 0.5 - 6 ml $^{99m}$Tc-eluate according to the desired activity dose is introduced with a disposable syringe into the vial containing the tin(II) chloride solution. The reaction solution is then swirled round gently in the vial and allowed to stand for about 5 minutes whereupon a stable tin-technetium-isocitrate complex is obtained. When sterile conditions are maintained the solution is ready for injection.

EXAMPLE 2

The tin(II)-isocitrate complex solution prepared as in example 1 is sterile filtered and 1.0 ml portions of the filtrate lyophilized in rubber-capped serum vials under an atmosphere of nitrogen. One vial contains the amount of substance required for one investigation.

To prepare a $^{99m}$Technetium-isocitrate complex, 0,5 - 6 ml $^{99m}$Tc-pertechnetate solution according to the desired activity dose is introduced under sterile conditions with a disposable syringe into the vial containing the lyophilized complex. Gentle swirling quickly dissolves the substance. The $^{99m}$Technetium-tin-isocitrate complex, ready for injection, is obtained quantitatively after about 5 minutes.

EXAMPLE 3

1.5 g cis-aconitic acid anhydride is dissolved in 10 ml water in a reaction vessel and warmed to 50° C. 30 mg tin(II) chloride is dissolved in this solution while stirring and passing nitrogen through the solution and the solution heated for about a further 10 minutes. The solution is then diluted to about 80 ml with water which has been purged with nitrogen, the pH adjusted to 5 ± 0.5 and the volume made up to 100 ml with nitrogen-purged water for injection.

The tri-tin-di-cis-aconitate complex solution is sterile filtered under an atmosphere of nitrogen and 1.0 ml portions of the filtrate are put into rubber-capped serum vials. The contents of these vials are lyophilized immediately.

To prepare a $^{99m}$Tc-cis-aconitate complex, 0.5 - 6 ml $^{99m}$Tc-pertechnetate solution is added to the lyophilized tri-tin-di-cis-aconitate complex in the rubber-capped serum vial. The liquid in the vial is swirled round a few times so that the pertechnetate dissolves and reacts more quickly with the lyophilized complex, and allowed to stand for about 5 minutes at room temperature. A clear, colourless solution, ready for injection, is obtained.

EXAMPLE 4

Using 3.0 g alpha-ketoglutaric acid instead of cis-aconitic acid the tin(II)-alpha-ketoglutarate complex is prepared by the method described in Example 3. Addition of $^{99m}$Tc-pertechnetate solution to the lyophilized complex gives the $^{99m}$Tc-tin-alpha-ketoglutarate complex.

EXAMPLE 5

The cis-aconitic acid used in the preparation described in Example 3 is replaced by 3 g oxalosuccinic acid. Addition of 0.5 - 6 ml $^{99m}$Tc-pertechnetate solution according to the required activity dose to the lyophilized tri-tin-di-oxalosuccinate complex gives the $^{99m}$Tc-tin-oxalosuccinate complex.

EXAMPLE 6

The cis-aconitic acid used in the preparation described in Example 3 is replaced by 1.5 - 4 g citric acid or sodium citrate or calcium citrate or iron(II) citrate or potassium citrate. A tri-tin-di-citrate complex or a tri-iron-tri-tin-tetracitrate complex is formed. After addition of $^{99m}$Tc-pertechnetate solution a technetium-iron-tin-citrate complex is formed in intravenously administerable form. The use of this co-complex is particularly preferred.

EXAMPLE 7

1.5 g citric acid is dissolved in 80 ml water for injection and the pH adjusted to 3.0 ± 0.1 with 2N sodium hydroxide solution. The volume of the solution is then made up to 100 ml and 1.0 ml portions introduced into rubber-capped serum vials. The pH of a 1.5N tris(hydroxymethyl)-aminomethane solution is adjusted to 8.5 with 2N hydrochloric acid, and 0.5 ml portions of this buffer solution introduced into the serum vials. The quantity of sterile, pyrogen-free reagent in each serum vial is sufficient for one investigation.

To prepare the $^{111}$indium-citrate complex, 4 ml $^{111}$In-eluate, corresponding to the desired activity dose, as indium chloride solution in an acid medium (0.04 - 0.07 N hydrochloric acid) is introduced into the rubber-capped serum vial with a disposable syringe, bringing the pH of the solution down to 2.4 - 2.5. The contents of an ampoule containing 0.5 ml 1.5N tris(hydroxymethyl)-aminomethane buffer solution is drawn up into the syringe and this is also added to the $^{111}$In-citric acid mixture. After the solution is swirled round an indium-citrate complex is obtained, the pH rising to 6.5 - 7.0. This complex is stable. The rubber-capped serum vial used as the reaction vessel remains sealed at all stages of the preparation; only the encysted rubber seal is pierced by the syringe needle. Such a solution containing $^{111}$Indium-citrate complex is ready for injection.

EXAMPLE 8

The citric acid used in Example 7 is replaced by 1.7 - 3 g sodium citrate or calcium citrate or iron(III) citrate and the pH adjusted to 3.0 ± 0.1 with 1N hydrochloric acid. After the addition of the radioactive indium chloride solution an indium complex is formed with radioactive indium as the metal ion and citrate ions as ligands.

EXAMPLE 9

10 ml of a 1M L-aspartic acid solution is mixed under nitrogen with 4 ml of a freshly prepared 0.1 M tin(II) chloride solution, the resulting solution diluted to 80 ml with nitrogen-purged distilled water and the pH adjusted to 6.5 ± 0.2 with 2N potassium hydroxide solution. Then the solution is made up to 100 ml, sterilized, and 1.0 ml portions are introduced into sterile 10 ml serum vials. After lyophilization the serum vials are sealed under sterile conditions with vacuum-stoppers and rim caps.

To prepare the $^{99m}$-Technetium-L-aspartate complex, 0.5 - 6 ml sterile $^{99m}$Tc-pertechnetate eluate, according to the required activity dose, is added to the contents of a serum vial with a disposable syringe by piercing the rubber vacuum-stopper with the syringe needle. The solution is swirled round gently and allowed to stand for about 5 minutes. The solution containing the $^{99m}$Technetium-L-aspartate complex is then drawn up into a syringe and used in the diagnosis of tumors by scintillation scanning.

EXAMPLE 10

30 mg solid tin(II) chloride is added to 20 ml of a 1% malic acid solution while stirring, and warmed to 60° for 10 minutes. After cooling, the solution is diluted to about 80 ml with distilled water, the pH adjusted to 5.5 ± 0.1 with 2N potassium hydroxide solution, the solution purged with nitrogen and made up to 100 ml. Subsequent procedure is as already described in Example 9.

EXAMPLE 11

1.5 g monopotassium L-aspartate (the monopotassium salt of L-aspartic acid) as the dihydrate is dissolved in 60 ml pyrogen-free distilled water and the pH adjusted to 2.5 ± 0.1 with 2N hydrochloric acid. The solution is then made up to 100 ml (pyrogen-free distilled water) and, after sterilization, 1.0 ml portions are introduced into sterile 5 ml serum vials. After lyophilization the serum vials are sealed under sterile conditions with vacuum-stoppers and rim caps.

To prepare the $^{111}$Indium-L-aspartate complex, 3 ml $^{111}$Indium eluate corresponding to the required activity dose, as indium chloride solution in an acid medium (0.05 ± 0.01N hydrochloric acid), is added to one of the serum vials with a disposable syringe. The pH of a sterile 1.5N tris(hydroxymethyl)-aminomethane solution is adjusted to 8.5 with 2N hydrochloric acid, and 0.5 ml of this solution added to the serum vial, thus shifting the pH-value to a physiologically harmless region. After swirling the solution round and allowing to stand for 5 minutes, the $^{111}$Indium-L-aspartate complex is ready for injection.

What is claimed is:

1. A process for producing a composition for the diagnostic visualization of neoplastic tissues, namely tumors and metastases, by means of tissue scintigraphy, consisting essentially of an injectable complex of $^{99m}$Technetium with a member selected from the group consisting of a dicarboxylic or tricarboxylic acid of the general formula:

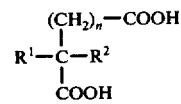

in which $n$ is 1 or 2, $R^1$ and $R^2$ taken together are an oxo group or the $>CH-COOH$ group or $R^1$ is a hydrogen atom or a hydroxyl or amino group and $R^2$ is a hydrogen atom or one of the following groups:

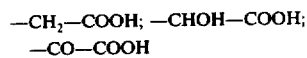

and a water-soluble salt of the same, in a sterile aqueous solution having a physiologically harmless pH value, said process consisting essentially of the steps of introducing an aqueous solution of a member selected from the group consisting of a dicarboxylic acid or tricarboxylic acid of the above formula and a water-soluble salt of the same into ampoules, rubber-capped serum vials, carpoules or disposable syringes, removing the solvent subsequently from the solution, reacting the intermediate product obtained which is in solid, stable form immediately before its use for diagnostic purposes with an aqueous solution containing the desired radioactivity dose of a $^{99m}$Technetium salt, oxygen being excluded, said injectable complex being produced such that it is in a sterile state.

2. A process as claimed in claim 1, wherein the dicarboxylic acid or tricarboxylic acid added is a member selected from the group consisting of isocitric acid, cis-aconitic acid, alpha-ketoglutaric acid, oxalosuccinic acid, citric acid, aspartic acid, oxaloacetic acid, malic acid and glutamic acid.

3. A process as claimed in claim 1, wherein the water-soluble salt added is the sodium, potassium or calcium salt and the complex obtained is in the form of a complex salt with the said cation.

4. A process as claimed in claim 1, wherein the pH is adjusted to a physiologically harmless value before reacting said intermediate product with said aqueous solution containing the desired radioactivity dose.

5. A process as claimed in claim 1, wherein the pH is adjusted to a physiologically harmless value after the reaction of said intermediate product with said aqueous solution containing the desired radio-activity dose.

6. A process for producing a composition for the diagnostic visualization of neoplastic tissues, namely tumors and metastases, by means of tissue scintigraphy, consisting essentially of an injectable complex of $^{99m}$Technetium and tin(II) with a member selected from the group consisting of a dicarboxylic or tricarboxylic acid of the general formula:

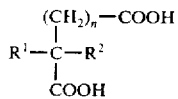

in which $n$ is 1 or 2, $R^1$ and $R^2$ taken together are an oxo group or the >CH—COOH group or $R^1$ is a hydrogen atom or a hydroxyl or amino group and $R^2$ is a hydrogen atom or one of the following groups:

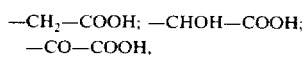

and a water-soluble salt of the same, in a sterile aqueous solution having a physiologically harmless pH value, said process consisting essentially of the steps of introducing an aqueous solution of a member selected from the group consisting of a dicarboxylic acid or tricarboxylic acid of the above formula and a water-soluble salt of the same and additionally a tin(II) salt into ampoules, rubber-capped serum vials, carpoules or disposable syringes, removing the solvent subsequently from the solution, reacting the intermediate product obtained which is in solid, stable form immediately before its use for diagnostic purposes with an aqueous solution containing the desired radioactivity dose of a $^{99m}$Tc-pertechnetate to form a co-complex with the tin ion.

7. A process for producing a composition for the diagnostic visualization of neoplastic tissues, namely tumors and metastases, by means of tissue scintigraphy, consisting essentially of an injectable complex of $^{99m}$Technetium and tin(II) with a member selected from the group consisting of a dicarboxylic or tricarboxylic acid of the general formula:

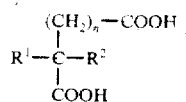

in which $n$ is 1 or 2, $R^1$ and $R^2$ taken together are an oxo group or the >CH—COOH group or $R^1$ is a hydrogen atom or a hydroxyl group or amino group and $R^2$ is a hydrogen atom or one of the following groups:

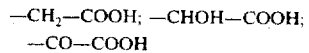

and a water-soluble salt of the same, in a sterile aqueous solution having a physiologically harmless pH value, said process consisting essentially of the steps of introducing an aqueous solution of a tin(II) complex of a member selected from the group consisting of a dicarboxylic or tricarboxylic acid of the above formula or a water-soluble salt of the same into ampoules, rubber-capped serum vials, carpoules or disposable syringes, removing the solvent subsequently from the solution, reacting the intermediate product obtained which is in solid, stable form immediately before its use for diagnostic purposes with an aqueous solution containing the desired radioactivity dose of a $^{99m}$Tc-pertechnetate to form a co-complex with the tin ion.

8. A process as claimed in claim 7, wherein the tin(II) complex added is a member selected from the group consisting of a tri-tin-di-isocitrate, tri-tin-di-cis-aconitate, tin alpha-ketoglutarate, tri-tin-di-oxalosuccinate, tri-tin-di-citrate, tri-iron-tri-tin-tetra-citrate, tin aspartate, tin oxaloacetate, tin malate and tin glutamate.

* * * * *